United States Patent
Silva et al.

(10) Patent No.: US 6,861,062 B2
(45) Date of Patent: *Mar. 1, 2005

(54) SKIN CREAM

(76) Inventors: Victor Silva, 1701 Cameron Ct., Edwardsville, IL (US) 62025; Andrew Szczesiul, 10831 Lawnbrook, St. Louis, MO (US) 63129; Gregory Rudroff, 336 6th St., Farmington, MO (US) 63640-2322

( * ) Notice: Subject to any disclaimer, the term of this patent is extended or adjusted under 35 U.S.C. 154(b) by 30 days.

This patent is subject to a terminal disclaimer.

(21) Appl. No.: 10/167,352

(22) Filed: Jun. 12, 2002

(65) Prior Publication Data

US 2002/0150597 A1 Oct. 17, 2002

Related U.S. Application Data

(63) Continuation-in-part of application No. 09/516,325, filed on Mar. 1, 2000, now Pat. No. 6,344,188.

(51) Int. Cl.$^7$ .................................................. A61K 7/48
(52) U.S. Cl. ........................ 424/401; 514/263; 514/944
(58) Field of Search ................................ 514/944, 263, 514/844, 846, 847, 969; 424/400, 401, 78.02, 78.03, 78.08

(56) References Cited

U.S. PATENT DOCUMENTS

| | | | |
|---|---|---|---|
| 5,296,241 A | * | 3/1994 | Brimberg et al. ........... 424/682 |
| 5,360,824 A | | 11/1994 | Barker |
| 5,626,854 A | | 5/1997 | Ichii et al. |
| 5,667,793 A | | 9/1997 | Cho |
| 5,922,331 A | | 7/1999 | Maysner |
| 6,344,188 B1 | * | 2/2002 | Silva et al. .............. 424/78.03 |

* cited by examiner

Primary Examiner—Thurman K. Page
Assistant Examiner—J. Venkat
(74) Attorney, Agent, or Firm—Don W. Weber

(57) ABSTRACT

A skin cream is presented which reduces wrinkles upon topical application to the skin. The main ingredients of the composition include water and a xanthine based compound composition which is mixed together in a first vessel and a glycerin composition heated in a second vessel. The three components of the active ingredient are mixed carefully, making sure that any precipitate produced is remixed into the solution. After heating and mixing the components, the entire composition is cooled with care being taken to push any precipitate back into solution to ensure an even distribution of all of the components. The active ingredient thus produced may be combined with a suitable pharmaceutical vehicle to provide the topical wrinkle reducing moisturizing and protecting composition. The composition is topically applied to the effected area over a period of days or months in order to reduce or entirely eliminate wrinkles and dryness from the skin. The final active ingredient may also be used for other applications.

7 Claims, No Drawings

SKIN CREAM

This application is a continuation-in-part of Ser. No. 09/516,325 filed Mar. 1, 2000, now U.S. Pat. No. 6,344,188.

BACKGROUND OF THE INVENTION

This invention relates to the field of skin care compositions. More particularly, a unique skin cream is presented which, when used topically, reduces wrinkles without the use of any abrasives or fillers and protects and moisturizes skin.

Cosmetics such as skin creams and moisturizing creams have been known in the art for hundreds of years. These creams or other moisturizers are applied to the skin in order to moisturize the skin and to prevent chapping or other undesirable conditions of the skin. On occasion, attempts have been made to create a cream or other pharmaceutical composition which will reduce wrinkles on the face, hands, and other areas of the skin. However, these compositions usually include abrasives which are used to scrape away the wrinkles on the skin. One such abrasive type cream is found in the 1994 patent issued to Barker.

Barker disclosed a human skin cleansing and wrinkle reducing cream comprised of soluble granules in a petroleum jelly or oil base. As described in Barker, the common practice in this art is to use abrading granules to strip off the wrinkled outer layer of skin. Skin abrading formulations are set out in the Barker patent. Barker himself discloses the use of "a plurality of water soluble, skin abrading granules or particles". It is an object of this invention to provide a wrinkle reducing cream which does not require the use of abrading granules or fillers which may irritate the skin.

Although some plant extracts and chemicals have been used in an attempt to create a suitable skin enhancing and protecting composition, most have met with limited success. A typical example of a skin care composition (used for treating cellulite) is found in the 1997 patent issued to Cho. This patent, U.S. Pat. No. 5,667,793, utilized certain exotic plant extracts as anti-cellulite agents. Cho utilizes a xanthine compound found in the exotic plant extracts to produce an anti-cellulite cream. Cho also discloses the topical application of his cream in order to eliminate or reduce cellulite. However, the general plant extracts used in Cho were designed to reduce cellulite rather than to eliminate wrinkles. Furthermore, the mere use of a xanthine compound, without the proper blending with other ingredients, leaves much to be desired with respect to the use of a member of the xanthine family to reduce wrinkles on the skin. It is a further object of this invention to provide a topical cream utilizing any member of the xanthine family in combination with water, glycerin and a suitable cosmetic vehicle to produce a wrinkle reducing cream.

U.S. Pat. No. 5,296,241 issued to Brimberg describes a hangover treatment cream comprising caffeine, glycerin, xanthine gum and purified water. As such, Brimberg constitutes a hangover treatment composition which has many of the same elements as found in the instant application. However, the unique method of blending the water, xanthine-based compound and glycerin together in the steps described later, including heating and cooling the solutions, produces an entirely new complex and active ingredient. It is an object of this invention to combine water, glycerin and a xanthine-based compound together in certain weight ratios, using certain method steps to create a new and novel skin cream composition which is capable of reducing skin wrinkles, protecting the skin, and moisturizing the skin.

U.S. Pat. No. 5,922,331 issued to Mausner also describes a therapeutic skin cream containing caffeine benzoate, caffeine, glycerol and de-ionized water. Mausner's composition, while containing many of the same elements as found in the instant application, contains ingredients which are separated from each other in three sets of microcapsules. Because Mausner's ingredients are kept separated, they do not interact with each other and do not produce a new molecule such as is produced by following the below-described method.

Xanthine derivatives have also been utilized as a bath composition to give a moist or fresh feeling to the skin and a warm feeling to the body. However, the combination of a xanthine compound with water, glycerin and a suitable cosmetic vehicle can also produce startling and new results, particularly with respect to the reduction of wrinkles on the skin. These new results are only obtained by combining the xanthine compound with water and glycerin brought to a particular consistency of composition by heating and cooling the various elements and combining them in particular proportions. It is a still further object of this invention to produce a wrinkle reducing cream by combining water, a xanthine based compound, and glycerin in a particular stepped method utilizing both heating and cooling of the component parts.

Although hydrous and anhydrous caffeine have been found to be a suitable ingredient to produce a wrinkle reducing, skin protecting and moisturizing compound, other xanthine or xanthine derivatives may be used in practicing this invention. A suitable xanthine based compound includes anhydrous theophylline, theobromine, theophylline monohydrate, hydrous and anhydrous aminophylline, dyphylline, oxtriphylline, caffeine citrate, and hydrous and anhydrous caffeine. These xanthine based compounds, when combined in particular proportions and using particular steps of heating, cooling, mixing and precipitating, can produce a new and unique skin cream which not only reduces wrinkles, but also protects and moisturized the skin. It is a still further object of this invention to produce a new compound, having a unique active ingredient, which has a salutary effect on the skin.

Other and further objects will become apparent upon reading the below described Specification.

SUMMARY OF THE INVENTION

A xanthine based compound selected from the group consisting of anhydrous theophylline, theobromine, theophylline monohydrate, hydrous and anhydrous aminophylline, dyphylline, oxtriphylline, caffeine citrate and hydrous caffeine is mixed with water and glycerin to form a topical cream. The xanthine based compound and water are mixed together first and may be heated to facilitate thorough mixing. Glycerin is heated in another vessel and is added to the xanthine based compound-water solution slowly. The entire composition is then cooled. Any precipitate coming out of the solution during cooling is pushed back into solution. The active ingredient for the topical skin cream is then produced. This active ingredient may then be combined with a suitable pharmaceutical vehicle to create the topical cream applied to the skin. The active ingredient may be utilized to reduce wrinkles and to protect and moisturize the skin.

DETAILED DESCRIPTION OF THE PREFERRED EMBODIMENT

The preferred embodiment includes a composition of xanthine based compound selected from the group consisting of anhydrous theophylline, theobromine, theophylline monohydrate, hydrous and anhydrous aminophylline, dyphylline, oxtriphylline, caffeine citrate, hydrous caffeine, water, and glycerin. These xanthine based compounds are often found in natural plant extracts. The natural plant extracts could be utilized. Extracts of green or black tea would produce theophylline and caffeine, extracts of coffee or gurana would produce caffeine and extracts of yerbamate would produce mateine. While green tea extracts are already used in some cosmetic products, they are commonly utilized to produce polyphenols not the theophylline or xanthine compounds. The three key components (xanthine based compound, water and glycerin) are combined in particular steps to produce the active ingredient. The new active ingredient is then combined with a suitable pharmaceutical vehicle to produce the finished topical skin cream.

It should be noted that this particular composition of ingredients contains no retinol. Although retinol has been tried in the past with respect to moisturizing and wrinkle reducing properties, retinol may cause harm to the end user. Since it is likely that women will use this wrinkle reducing cream, it would be highly desirable to develop a skin cream without using retinol. It is a still further object of this invention to provide a skin cream which does not utilize retinol as an ingredient in the final composition.

In selecting the particular xanthine based compound to be used in practicing this invention, various weights of the xanthine based compound would be utilized. For example, when combining the xanthine compound with 60 ml of water and ultimately 167 grams of glycerin, the following weights of a xanthine based derivative would be used: theophylline-74 grams; theobromine-74 grams; theophylline monohydrate-81 grams; anhydrous aminophylline-87 grams; hydrous aminophylline-96 grams; diphylline-105 grams; oxtriphylline-115 grams; hydrous caffeine-80 grams; and caffeine citrate-148 grams. Thus, in combining between 74 to 148 grams of a xanthine based compound, as set out above, one could create the active ingredient used for a wrinkle reducing, moisturizing and skin protecting cream.

The preferred procedure for making the active ingredient of this disclosure involves nine steps, combining and heating the various components to produce the final composition. The steps to be followed in producing this active ingredient are as follows.

1. Into a first vessel, one places 60 ml of water, in proportion, and 74 to 148 grams of a xanthine based compound, as indicated above, in proportion. This vessel may be heated to facilitate thorough mixing.
2. The xanthine based compound and water are mixed together. At the same time the temperature of this mixture may be brought up to approximately 70 degrees Centigrade.
3. The water and xanthine based compound are slowly stirred to produce a homogenous mixture.
4. While the water-xanthine based compound mixture is being prepared, a second vessel containing 167 grams of glycerin, in proportion, is heated.
5. The glycerin in the second vessel is heated to a temperature of approximately 70 degrees Centigrade.
6. Once the glycerin is heated to 70 degrees Centigrade, the glycerin is slowly added to the water-xanthine based compound mixture. This is accomplished by slowly stirring the glycerin as it is added to the first vessel containing the water-xanthine based compound mixture.
7. The water-xanthine based compound and glycerin compositions are slowly mixed for approximately one and one-half minutes, while any precipitate is pushed back into the mixture.
8. After mixing the composition for approximately one and one-half minutes, the mixture is removed from heat and allowed to cool at room temperature. A cold water bath can be used to speed up the precipitation and cooling process.
9. A precipitate may be produced as the mixture is cooled and comes out of the solution. Any precipitate must be mixed back into the entire solution in order to keep all components evenly distributed throughout the final composition.

These nine steps produce the active ingredient. This active ingredient may then be combined with a suitable cosmetic or pharmaceutical vehicle to produce the topical skin cream. In the production of this particular active ingredient, the general parameters set out above could be combined to produce approximately 250–350 grams of the active ingredient. The actual yield of the final composition would depend on the total weight of the ingredients used less the amount of water lost during the heating process.

During this process, most of the water is lost due to evaporation. Using the weights indicated above (60 ml or grams of water, 74–148 grams of a xanthine based compound and 167 grams of glycerin) the final active ingredient would contain approximately 4% by weight of water, 29.5% by weight of a xanthine based compound and 66.5% by weight of glycerin.

The above weights are meant as an illustration only and not as a limitation. The amounts of water, a xanthine based compound, and glycerin are proportional and approximate. For example, one could produce approximately 2,500 grams of active ingredient by adding 600 ml of water, 740 grams of theobromine or, for example 960 grams of hydrous aminophylline, and then mixing with 1,670 grams of glycerin.

Certain broad parameters can be described in practicing this invention which will produce an effective active ingredient. The above weights of water, a xanthine based compound, and glycerin are meant as a means of illustration only and not as a limitation. The general weight ranges to produce a satisfactory active ingredient would vary, depending upon the xanthine based compound used. For example, using 60 ml of water and 167 grams of glycerin, one would use 74 grams of anhydrous caffeine, anhydrous theophylline, or theobromine. 87.3 grams of anhydrous aminophylline would be used and 96.2 grams of hydrous aminophylline would be used. 105.1 grams of diphylline would be required and 115.4 grams of oxitriphylline would be required. 148 grams of caffeine citrate would be used with 60 ml of water and 167 grams of glycerin while 80.7 grams of hydrous caffeine would be required. Since these weights are proportional, each of the weights of the xanthine based compound, water, and glycerin could be multiplied by a factor of 5, 10, or any other factor to achieve the desired amount of active ingredient.

The following parameters can be used in producing the active ingredient. Generally, the active ingredient can be produced by mixing the following range of components by weight at the temperatures indicated:

1. The amount of water used in the first vessel could be between 90 ml to 900 ml. To that could be added between 10 grams to 1200 grams of a xanthine based compound selected from the group consisting of anhydrous theophylline, theobromine, theophylline monohydrate, hydrous and anhydrous aminophylline, dyphylline, oxtriphylline, caffeine citrate, and hydrous caffeine.

2. The water-xanthine based compound mixture may be heated to between 48.8 degrees Centigrade to 115 degrees Centigrade in the first vessel to facilitate mixing.
3. These components should be mixed until the xanthine based compound goes into solution.
4. The glycerin to be added to the first vessel would range from between 45 grams to 540 grams of glycerin.
5. The temperature range for heating the glycerin in the second vessel can be from 10 degrees Centigrade to 115 degrees Centigrade.
6. Once these two vessels have been prepared, the glycerin is added to the water-xanthine based compound composite mixture slowly.
7. In order to mix the water-xanthine based compound and glycerin components, approximately one and one-half minutes are required. Any precipitate should be pushed back into solution. However, these three components can be mixed from between 15 seconds to 10 minutes to still produce a suitable final composition.
8. The combined final composite mixture is then allowed to cool.
9. As the above mixture is cooled, the precipitate should be mixed back into the whole in order to keep all components evenly distributed throughout the mass of the active ingredient.

The active ingredient produced by this method will produce an active ingredient containing water, a xanthine based compound, and glycerin. It has been found that the following range of percentages by weight of each of the initial components produces a satisfactory final active ingredient: Final Percentage by Weight—xanthine based compound-7% to 50% by weight; glycerin 14% to 60% by weight; the remainder of the composition would be water.

The percentage by weight of water, a xanthine based compound and glycerin set out above produce a suitable active ingredient having wrinkle reducing and other properties.

Once the active ingredient has been produced, it should be combined with a suitable cosmetic or pharmaceutical vehicle which would normally be some type of ointment base. Suitable cosmetic vehicles may include hydrophilic ointments, petrolatums such as Vaseline™, Dermabase™, lotions or gels, or standard cold creams found commonly in the market. In normal practice the active ingredient would be heated and combined with the suitable cosmetic base to produce the final composite cream. It is the active ingredient which forms the essence of this new composition of matter.

The active ingredient has a unique chemical structure. Due to the unique steps followed in combining the xanthine based compound, water and glycerin a number of unusual and unexpected characteristics are produced. The heating and cooling of the ingredients, as well as their combination, creates the unique active ingredient complex. Rather than merely creating an amalgam of separate parts (water, glycerin and xanthine compound), the ingredients in the instant composition interact with one another chemically to form a totally unique complex. Utilizing this particular method, the xanthine based compound is a water soluble ingredient, unlike the non-soluble caffeine and xanthine based compounds found in the prior art. The elevation of the temperature to approximately 168 degrees Fahrenheit (70 degrees Centigrade) causes a faster reaction and precipitates out the active ingredient complex more quickly. Since the active ingredient complex forms only minimally at room temperature, the added step of heating the combined new complex greatly enhances the process of producing the active ingredient. It is only when the xanthine based compound is dissolved in the heated water, and glycerin is then added to the water-xanthine based compound mixture that useful quantities of the active ingredient complex are obtained. If the xanthine based compound-water solution were allowed to cool before adding the glycerin, the xanthine based compound would recrystalize and fall out of solution as the solution is cooled, before the glycerin could be added. It can thus be seen that the heating steps, as well as the step of adding the glycerin after the compound is heated, as well as the cooling step, are critical to the production of a new, unique, and readily produced active ingredient.

When the glycerin is added to the heated water-xanthine based mixture, the xanthine based compound and glycerin form a new chemical complex that precipitates out of solution and forms a smooth amorphic gelatinous mass. This amorphic gelatinous mass differs from the prior art in a number of significant ways. The instant compound utilizes a much larger amount of the xanthine based compound by weight. For example, the xanthine based compound could be twenty to thirty-five times larger than the amount of caffeine or other xanthine based compounds currently in use. The xanthine based compound is water soluble, while the xanthines used in other compounds generally are not. Most importantly, the xanthine based compound, when produced by the method described herein, creates a unique xanthine based chemical complex rather than xanthine being merely one part of a non-homogenous mixture. The heat causes the chemical reaction in the instant process. Without it, the instant method and composition would not produce the unique active ingredient complex described herein.

It has been found that the combination of water, a xanthine based compound and glycerin, obtained through the procedures as described above, produces a highly effective skin cream capable of reducing or eliminating wrinkles when topically applied. It also could be used to recondition dry, chapped skin, skin exposed to the wind or the sun, to protect the skin before or after sun or wind exposure, to treat skin conditions due to the natural aging process, and as an agent to be used before or after ultraviolet radiation exposure. As a moisturizing agent, the composition including the active ingredient may be used to provide moisture to the skin. As such it could be used to treat conditions of the skin such as dry skin, eczema, psoriasis, for exposure of the skin to wind or sun, for dry skin due to the natural aging process and to provide moisture and to enhance the natural moisture barrier of the body.

The instant composition is an improvement over those compositions involving a xanthine based compound alone or a xanthine based compound in composition with other cosmetic vehicles. Xanthine based compound compositions alone would readily dissolve in water, whereas the instant composition is not readily soluble in water. This is important as the instant composition will not deteriorate or wash off during bathing or heavy sweating. Another salutary effect of the instant device is that when water is applied to it, it reactivates the composition rather than dissolving it.

After much experimentation it has been found that the use of glycerin to combine with the xanthine based compound is important since glycerin is much more suitable than animal fat or any other dissolving agent. Glycerin is more stable than animal fat and will not allow the xanthine based compound to penetrate into the actual cells sought to be treated with this final compound. When the water-xanthine based compound-glycerin components are mixed and heated as described above, the end result is a highly desirable skin cream that has been effective in actual clinical tests in reducing wrinkles, and protecting and moisturizing the skin.

It is thought that the instant composition provides the salutary effects of a wrinkle reducing cream, skin protectorate and moisturizer by strengthening the cell membrane and coating the cell membranes with strands of fat to protect cells which would otherwise produce wrinkles or dry, chapped skin. Although the exact mechanism action of this new composition has not been determined, experimentation has shown that the combination of water, xanthine based compound and glycerin, when heated, mixed, and cooled, as outlined above, will produce a cream which will reduce wrinkles and protect and moisturize the skin.

The final composite cream should be applied twice daily to the effected areas of the skin. Results have been seen as soon as 24 hours after a first application, although the best results are obtained over a period of days or months of application of the skin cream.

We claim:

1. A method of producing a skin care composition, comprising the steps of:
    1) placing between 90 ml to 900 ml of water and 10 grams to 1200 grams of a xanthine based compound selected from the group consisting of anhydrous theophylline, theobromine, theophylline monohydrate, hydrous and anhydrous aminophylline, dyphylline, oxtriphylline, caffeine citrate, and hydrous caffeine into a first vessel;
    2) heating the water and xanthine based compound mixture to between 48.8 to 115 degrees Centigrade;
    3) slowly mixing the water and xanthine based compound together until the xanthine based compound goes into solution;
    4) placing between 45 grams to 540 grams of glycerin into a second vessel;
    5) heating the second vessel containing the glycerin to a temperature range between 10 degrees Centigrade and 115 degrees Centigrade;
    6) slowly adding the heated glycerin in vessel 2 to the water-xanthine based compound mixture in vessel 1 while stirring the composite mixture;
    7) mixing the water, xanthine based compound and glycerin components slowly for a certain period of time, ranging between 15 seconds to 10 minutes, while pushing any precipitate back into the mixture;
    8) removing the resulting final composite mixture from the heat and allowing it to cool to room temperature;
    9) mixing any precipitate that develops in Step 8 back into the composition in order to keep the precipitate evenly distributed, producing the active ingredient herein;
    10) combining the resulting active ingredient with a suitable cosmetic or pharmaceutical vehicle to produce a topical cream;
    wherein said water-xanthine based compound and glycerin chemically interact to create a final active ingredient.

2. A method of producing a skin care composition, comprising the steps of:
    1) placing, in proportion, 60 ml of water and 74 to 148 grams of a xanthine based compound into a first vessel;
    2) mixing the water and xanthine based compound components together;
    3) slowly mixing the water and xanthine based compound together in the first vessel until a homogenous mixture is obtained;
    4) placing, in proportion, 167 grams of glycerin into a second vessel;
    5) heating the second vessel containing the glycerin to 70 degrees Centigrade;
    6) slowly adding the heated glycerin in vessel 2 to the water-xanthine based compound mixture, while stirring the resulting composite mixture;
    7) mixing the water, xanthine based compound and glycerin components slowly for one and one-half minutes while pushing any precipitate back into the mixture;
    8) removing the resulting composite mixture from the heat and allowing it to cool to room temperature;
    9) mixing any precipitate that develops in Step 8 back into the composite mixture in order to keep the precipitate evenly distributed, producing the active ingredient herein;
    10) combining the resulting active ingredient with a suitable cosmetic or pharmaceutical vehicle to produce a topical cream;
    wherein said water, xanthine based compound and glycerin chemically interact to create a final active ingredient.

3. A method of producing a skin care composition as in claim 2, wherein said first vessel containing the water-xanthine based compound mixture may be heated to approximately 70 degrees Centigrade to facilitate mixing.

4. The method of producing a skin care composition as in claim 1, wherein said suitable cosmetic or pharmaceutical vehicle includes a hydrophilic ointment, a petrolatum, a lotion or gel.

5. A method of producing a skin care composition as in claim 2, wherein said suitable pharmaceutical vehicle includes a hydrophilic ointment, a petrolatum, a lotion or gel.

6. A composition, consisting of:
    1. Between 4% to 72% by weight of water;
    2. Between 7% to 50% by weight of a xanthine based compound selected from the group consisting of anhydrous theophylline, theobromine, theophylline monohydrate, hydrous and anhydrous aminophylline, dyphylline, oxtriphylline, caffeine citrate, and hydrous caffeine mateine;
    3. Between 14% to 60% by weight of glycerin;
    wherein said water and xanthine based compound are placed in a first vessel and mixed together and wherein said glycerin is heated in a second vessel and then added to said water and caffeine mixture and then cooled;
    whereby said water, xanthine based compound and glycerin chemically interact to create a final active ingredient.

7. A composition of matter as in claim 6, wherein said composition consists of 7% to 50% be weight of a xanthine based compound, 14% to 60% by weight of glycerin; and wherein the remainder is water; and wherein said water and xanthine based compound are placed in a first vessel and mixed together and wherein said glycerin is heated in a second vessel and then added to said water and Xanthine mixture and then cooled;
    wherein said water, xanthine based compound and glycerin chemically interact to create a final active ingredient.

* * * * *